United States Patent [19]
Olesen

[11] Patent Number: 5,859,004
[45] Date of Patent: Jan. 12, 1999

[54] USE OF HETEROCYCLIC COMPOUNDS FOR THE TREATMENT OF CONDITIONS CAUSED BY MALFUNCTIONING OF THE NICOTINIC CHOLINERGIC SYSTEM

[75] Inventor: Preben Houlberg Olesen, Coppenhagen NV, Denmark

[73] Assignee: Novo Nordisk A/S, Bagsvaerd, Denmark

[21] Appl. No.: 875,834

[22] PCT Filed: Feb. 12, 1996

[86] PCT No.: PCT/DK96/00069

§ 371 Date: Aug. 6, 1997

§ 102(e) Date: Aug. 6, 1997

[87] PCT Pub. No.: WO96/25160

PCT Pub. Date: Aug. 22, 1996

[30]   Foreign Application Priority Data

Feb. 17, 1995 [DK] Denmark .................................. 0176/95

[51] Int. Cl.$^6$ ............................. A61K 31/55; A61K 31/44
[52] U.S. Cl. ........................... 514/214; 514/299; 514/305
[58] Field of Search ................................... 514/214, 299, 514/305

[56]   References Cited

FOREIGN PATENT DOCUMENTS

| | | |
|---|---|---|
| 0307142 A1 | 3/1989 | European Pat. Off. . |
| 0363085 A2 | 4/1990 | European Pat. Off. . |
| 0414394 A2 | 2/1991 | European Pat. Off. . |
| 0458214 A1 | 11/1991 | European Pat. Off. . |
| 9203433 A1 | 3/1992 | WIPO . |

*Primary Examiner*—William R. A. Jarvis
*Attorney, Agent, or Firm*—Steve T. Zelson; Valeta Gregg; Carol E. Rozek

[57]   ABSTRACT

This invention relates to the use of azabicyclic compounds for the treatment of diseases caused by malfunctioning of the nicotinic cholinergic system. These diseases treated include obesity, Parkinson's disease, anxiety, and ulcerative colitis.

10 Claims, No Drawings

USE OF HETEROCYCLIC COMPOUNDS FOR THE TREATMENT OF CONDITIONS CAUSED BY MALFUNCTIONING OF THE NICOTINIC CHOLINERGIC SYSTEM

CROSS-REFERENCE TO RELATED APPLICATIONS

This application is a 35 U.S.C. 371 national application of PCT/DK96/00069 filed Feb. 12, 1996, and claims priority under 35 U.S.C. 119 of Danish application 0176/95 filed Feb. 17, 1995, the contents of which are fully incorporated herein by reference.

FIELD OF THE INVENTION

The present invention relates to the use of heterocyclic compounds which are cholinergic ligands selective for neuronal nicotinic channel receptors in treating cognitive, neurological and mental disorders, such as dementia and anxiety, which are characterized by decreased cholinergic function.

The invention also relates to a method of treating Parkinson's disease by modulating the process of dopamine secretion, a method of treating or preventing withdrawal symptoms caused by cessation of chronic or long term use of tobacco products, as well as a method for treating obesity.

Further, the invention relates to pharmaceutical compositions of the compounds.

BACKGROUND OF THE INVENTION

Nicotinic and muscarinic receptors are the two distinct types of cholinergic receptors named after their selectivity for muscarine and nicotine, respectively. The cholinergic system is the neurotransmitter system that best correlates with memory and cognitive functions. Traditionally, the cholinergic hypothesis for senile dementia of the Alzheimer type (SDAT) has focused on muscarinic acetylcholine receptors (mAChR), and only recently an interest in the role of the nicotinic acetylcholine receptors (nAChR) in SDAT has emerged. This interest was spurred by the relatively recent discovery that nAChR are not only located on the skeletal muscle but also in the brain.

It has been shown that the number of nAChR were decreased in SDAT patients (Nordberg et al. J. Neurosci. Res.Vol. 31, pp. 103–111 (1992); Giacobini Advances in Experimental Medicine and Biology, Vol. 296, pp.9205–9295, (1993); Schroeder et al., Neurobiol. of Aging, Vol. 12, pp. 259–262, (1991); Whitehouse et al., Neurology, Vol. 38, pp. 720–723, (1988); Flynn and Mash, J. Neurochem., Vol. 47, pp. 8702–8702, (1993)). Similar deficiencies in choline acetyltransferase activity and acetylcholine synthesis suggest that presynaptic receptors on cholinergic nerve terminals are preferentially lost in SDAT (Nordberg, J. Reprod. Fert. Suppl., Vol 46, pp. 145–154, (1993)). Therefore, it has been assumed that the loss of nAChR may correlate with age related onset of disorders of memory and cognitive functions, and that nicotinic replacement therapy may prove beneficial in SDAT. Indeed nicotine improved attention and memory in healthy humans (Warburton, Prog. Neuro. Psychopharmacol. Biol. Psychiatry, Vol. 16, pp. 181–191, (1992)) as well as in Alzheimer's disease patients, (Jones et al. Psychopharmacology, Vol. 108, pp. 485–494, (1992); Gitelman and Prohovnik, Neurobiol. of Aging, Vol. 13, pp. 313–318, (1992); Newhouse et al., Psychopharmacology, Vol. 95, pp. 171–175, (1988); Sahakian et al., Br. J. Psychiatry, Vol.154, pp. 9004–904, (1993)). Further the nicotinic antagonist mecamylamine has been shown to cause cognitive impairment in an age related way, (Newhouse et al., Neuropsychopharmacology, Vol 10, pp. 93–107, (1994)).

Parkinson's disease (PD) is a debilitating neurodegenerative disease, presently of unknown etiology, characterized by tremors and muscular rigidity. There is evidence that nicotine may also have beneficial effects in PD. Studies show that smoking may protect against the development of PD, (Ishikawa and Mmiyatake, J. Neurol. Sci., Vol. 117, pp. 28–32, (1993); Godwin-Austen et al., J. Neurol. Neurosurg. Psychiat., Vol. 45, pp. 577–581, (1982); Reavill, in Nicotine psychopharmacology: Molecular, cellular and behavioral aspects, pp. 307–340, Oxford University Press, (1990)), and that chronic nicotine may protect against cell loss in the substantia nigra caused by lesioning (Janson and Moller, Neuroscience, Vol. 57, 931–941, (1993)). Nicotine has also shown beneficial effects in Tourette's syndrome (Sanberg et al., Biomed. Phamacother., Vol. 43, pp. 19–23, (1989)). Alleviation of negative psychotic symptoms, known as the hypofrontality syndrome in schizophrenia, by nicotinic agonists, have been suggested by data showing that nicotine stimulates dopamine release in the nucleus accumbens more potently than in striatum, (Rowell et al. J. Neurochem., Vol. 49, pp. 1449–1454, (1987); Giorguieff-Chesselet et al., Life Sciences, Vol. 25, pp. 1257–1262, (1979)), by nicotinic reversal of inactivation of prefrontal neurons (Svenson et al., In the Biology of Nicotine dependence., pp. 169–185, New York, (1990)), and by the observation that nicotine will potentiate dopaminergic effects in various behavioral models, (Reavill, in Nicotine psychopharmacology: Molecular, cellular and behavioral aspects, pp. 307–340, Oxford University Press, (1990); Rosecrans et al., Psychopharmacol. Commmun., Vol. 2, pp. 349–356, (1976); Reavill and Stolerman, J. Psychopharmacol., Vol. 1, pp. 264, (1987)).

In recent years there have been several studies on the effects of nicotine and food consumption and associated changes in body weight in rat and human. (Greenberg et al., Addictive behaviours, Vol. 7, pp. 317–331, (1982) and Greenberg et al., Psychopharmacology, Vol. 90, pp. 101–105, (1984)). The appetite effects of nicotine have been suggested to be mediated via modulation of CCK peptides in the paraventricular hypothalamic nucleus (Fuxe et al., Acta Physiologica Scandinavica, Vol. 125, pp. 437–443, (1985)).

EP 414394 discloses a class of methyleneazabicyclic compounds, substituted with a five membered heterocyclic ring described as cholinergic compounds which enhance acetylcholine function via an action at muscarinic receptors within the central nervous system.

DESCRIPTION OF THE INVENTION

It is an object of the invention to provide the use of heterocyclic compounds with affinity and selectivity for nicotinic cholinergic receptors in treating Alzheimer's disease, Parkinson's disease, Tourette's syndrome, ulcerative colitis, obesity, other central nervous system and gastrointestinal disorders as well as severe pain and pharmaceutical compositions of the compounds.

The method of this invention comprises administering to a patient suffering from a disease caused by malfunctioning of the nicotinic cholinergic system an effective amount of a compound of formula I

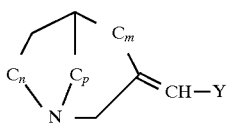

(I)

wherein
p is 1 and either m is 0 and n is 1 or 2 or m is 1 and n is 1, or p is 2, m is 0 and n is 1; and
wherein
Y is

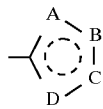

(a)

wherein
-A-B-C-D- is selected from =C(R$^1$)—O—N=C(R$^2$)—, =C(R$^1$)—S—N=C(R$^2$)—, =C(R$^1$)—N=C(R$^2$)—O—, =C(R$^1$)—C(R$^2$)=C(R$^3$)—O—, =C(R$^1$)—C(R$^2$)=N—O—, =C(R$^1$)—N=C(R$^2$)—S—, =C(R$^1$)—C(R$^2$)=C(R$^3$)—S—, =C(R$^1$)—C(R$^2$)=N—S—, —C(R$^1$)=C(R$^2$)—O—C(R$^3$)=, —C(R$^1$)=C(R$^2$)—S—C(R$^3$)=, —N(R$^4$)—N=C(R$^1$)—C(R$^2$)=, =N—N(R$^4$)—C(R$^1$)=C(R$^2$)—, =N—O—C(R$^1$)=C(R$^2$)—, =N—S—C(R$^1$)=C(R$^2$)—, —N(R$^4$)—C(R$^1$)=N—C(R$^2$)=, —N=C(R$^1$)—N(R$^4$)—C(R$^2$)=, =C(R$^1$)—N(R$^4$)—N=C(R$^2$)—, —N=C(R$^1$)—O—C(R$^2$)=, —N=C(R$^1$)—S—C(R$^2$)=, =N—C(R$^1$)=C(R$^2$)—N(R$^4$)—, =N—C(R$^1$)=C(R$^2$)—O—, =N—C(R$^1$)=C(R$^2$)—S—, —N(R$^4$)—N=N—C(R$^1$)=, =N—N(R$^4$)—N=C(R$^1$)—, —N=N—N(R$^4$)—C(R$^1$)=, —N(R$^4$)—N=C(R$^1$)—N=, =N—N(R$^4$)—C(R$^1$)=N—, =N—N=C(R$^1$)—N(R$^4$)—, =N—O—N=C(R$^1$)—, =N—N=C(R$^1$)—O—, —N=C(R$^1$)—O—N=, =N—C(R$^1$)=N—O—, =N—N=C(R$^1$)—S—, =N—S—N=C(R$^1$)—, —N=C(R$^1$)—S—N=, —N(R$^4$)—N=N—N=, =N—N(R$^4$)—N=N—; and
R$^1$, R$^2$ and R$^3$ independently are hydrogen, halogen, NR$^5$R$^6$, C$_{2-3}$-alkenyl, C$_{2-3}$-alkynyl or C$_{1-2}$-alkyl optionally substituted with one, two or three fluorine atoms; and
R$^4$ is C$_{1-2}$-alkyl, cyclopropyl or propargyl; and
R$^5$ and R$^6$ independently are hydrogen or methyl, or a pharmaceutically acceptable salt thereof.

In a preferred embodiment of the invention -A-B-C-D- is selected from
=C(R1)—C(R2)=N—O—,
=C(R1)—C(R2)=N—S—,
=N—O—C(R1)=C(R2)—,
=N—S—C(R1)=C(R2)—.

These compounds have a preferred selectivity for nicotinic receptors as compared to muscarinic receptors. This selective affinity makes them useful for treatment of diseases caused by malfunctioning of the nicotinic cholinergic system such as e.g. obesity, Parkinson's disease, anxiety, Alzheimer's disease and ulcerative colitis.

The term "C$_{1-2}$-alkyl" as used herein refers to a saturated hydrocarbon chain having from one to two carbon atoms such as e.g. methyl and ethyl.

The term "C$_{2-3}$-alkenyl" as used herein refers to an unsaturated hydrocarbon chain having from two to three carbon atoms and one double bond such as e.g. vinyl, 1-propenyl, allyl and isopropenyl.

The term "C$_{2-3}$-alkynyl" as used herein refers to unsaturated hydrocarbons which contains triple bonds such as e.g. —C≡CH, —C≡CCH$_3$ and —CH$_2$C≡CH.

The term "halogen" means fluorine, chlorine, bromine or iodine.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in Journal of Pharmaceutical Science, 66, 2 (1977) which are hereby incorporated by reference.

The compounds used in this method may be prepared using the methods taught in EP 414394, which are hereby incorporated by reference. Further, the example material of EP 414394 is also hereby incorporated by reference. The following description is intended to illustrate possible synthetic routes for the preparation of the compounds utilized in this method.

The compounds may be prepared by
a) reacting a compound of formula II

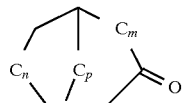

(II)

wherein m, n and p have the meanings defined above with a phosphorus ylide of formula III or IV

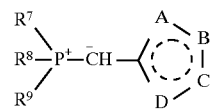

III

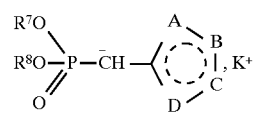

IV wherein R$^7$, R$^8$ and R$^9$ independently are C$_{1-6}$-alkyl, aryl or aralkyl and -A-B-C-D- has the meaning defined above, to give a compound of formula I, or
b) reacting a compound of formula II with a compound of formula V

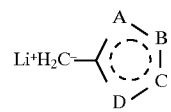

(V)

wherein -A-B-C-D- has the meaning defined above, followed by a dehydration to give compound of formula I.

It is to be understood that the invention extends to each of the stereoisomeric forms of the compound of formula I as well as the racemates.

The pharmacological properties of the compounds of the invention can be illustrated by determining their capability to inhibit the specific binding of $^3$H-methylcarbamylcholine ($^3$H-MCC) (Abood and Grassi, Biochem. Pharmacol., Vol. 35, pp. 4199—4202, (1986)).

$^3$H-MCC labels the nicotinic receptors in the CNS. The inhibitory effect on $^3$H-MMC binding reflects the affinity for nicotinic acetylcholine receptors.

Fresh or frozen rat, brain tissue (hippocampus or cortex) was homogenized in assay buffer (50 mM Tris-HCl, pH 7.4, 120 mM NaCl, 5 mM KCl, 2 mM CaCl$_2$, 1 mM MgCl$_2$) and centrifuged for 10 min. at 40.000×g. Pellets were subsequently reconstituted in assay buffer and an appropriate amount of tissue sample was mixed in tubes with $^3$H-methylcarbamylcholine (NEN, NET-951; final concentration 2 nM) and test drug. The tubes were incubated at 0° C. for 60 min. Unbound ligand was separated from bound ligand by vacuum filtration through GF/B filters presoaked in 0.5% polyethylenimine. Filters were washed three times with 5 ml wash buffer (50 mM Tris-HCl, pH 7.4) and transferred to vials. 4 ml scintillation fluid was added and the radioactivity was measured by scintillation counting. Unspecific binding was measured with 10 µM nicotine.

The $IC_{50}$ values of the test compounds were determined by nonlinear regression analyses (GraphPad InPlot).

Furthermore, the pharmacological properties of the compounds of the invention can also be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0°–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 µl of test solution and 25 µl of $^3$H-Oxotremorine (1.0 nM, final concentration) mixed and incubated for 30 min. at 25° C. Non-specific binding is determined in triplicate using arecoline (1 µg/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam-bath for less than 5 min.) at a concentration of 2.2 mg/ml. 25–75% inhibition of specific binding must be obtained before calculation of $IC_{50}$. The test value will be given as $IC_{50}$ (the concentration (nM) of the test substance which inhibits the specific binding of $^3$H-Oxo by 50%).

$$IC_{50}=\text{(applied test substance concentration)} \times (C_x/C_o-C_x) nM$$

where $C_o$ is specific binding in control assays and $C_x$ is the specific binding in the test assay. (The calculations assume normal mass-action kinetics).

Table I illustrates the affinity of the compounds of the present invention for nicotinic and muscarinic receptors as determined by $^3$H-MCC and $^3$H-Oxo binding to rat cortical receptors. The compounds, however, show selective affinity for nicotinic receptors as compared to muscarinic receptors, i.e OXO/MCC>1.

TABLE 1

| Compound | $^3$H-MCC $IC_{50}$ nM | $IC_{50}$ nM | $^3$H-Oxo Ratio | Oxo/MCC |
|---|---|---|---|---|
| 3 | 161 | 953 | 5.9 | |
| 4 | 81 | 1779 | 22.1 | |
| 5 | 25 | 430 | 17.2 | |
| 6 | 20 | 1100 | 55.0 | |

The compounds of the invention are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from diseases in the central nervous system caused by malfunctioning of the nicotinic cholinergic system it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intraurethral, intramuscular, intranasal, ophthalmic solution or an ointment, the oral route being preferred.

Typical compositions include a compound of formula I or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxy-ethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| Active compound | 5.0 mg |
|---|---|
| Lactosum | 67.8 mg Ph. Eur. |
| Avicel ® | 31.4 mg |
| Amberlite ® | 1.0 mg |
| Magnesii stearas | 0.25 mg Ph. Eur. |

The invention will now be described in further detail with reference to the following examples:

EXAMPLE 1

3-Hydroxy-3-(3-methyl-5-isoxazolyl) methyl-1-azabicyclo[2.2.2]octane

To a solution of 3,5-dimethylisoxazole (9.71 g, 100 mmol) in dry tetrahydrofuran (30 ml) cooled to −78° C. was added n-BuLi (2.5M in hexane, 100 mmol). The reaction mixture was stirred at −78° C. for 1 h. A solution of 3-quinuclidinone (6.25 g, 50 mmol) dissolved in dry tetrahydrofuran (50 ml) was added. The reaction mixture was stirred for 2 h at −78° C., then quenched with water (100 ml) and acidified with concentrated hydrochloric acid. The water phase was extracted with ether (2×50 ml), then basified with solid potassium carbonate and extracted with methylene chloride (4×100 ml). The methylene chloride phases were collected and dried over magnesium sulfate. After evaporation of the solvent the title compound was isolated in 10.04 g. 90% yield.

(Z)-3-(3-methyl-5-isoxazolyl)methylene-1-azabicyclo[2.2.2]octane oxalate and (E)-3-(3-methyl-5-isoxazolyl)methylene-1-azabicyclo[2.2.2]octane oxalate To a solution of 3-Hydroxy-3-(3-methyl-5-isoxazolyl) methyl-1-azabicyclo-[2.2.2]octane (10.04 g, 45 mmol) in methylene chloride (100 ml) was added triethylamine (8.9 g, 100 mmol). The reaction mixture was cooled to 0° C., and thionyl chloride (16.06 g, 135 mmol) in methylene chloride (50 ml) was carefully added. The reaction mixture was stirred at 0° C. for 1 h and then poured on ice. The phases were separated and the water phase basified with solid potassium carbonate. The water phase was extracted with ether (4×100 ml). The ether phases were dried over magnesium sulfate and evaporated giving a crude mixture of Z and E isomers. The title compounds were purified by column chromatography (eluent: ethyl acetate/methanol/ammoniumhydroxide: 2/1/2%).

The first fractions contained the Z isomer which after crystallisation with oxalic acid gave (Z)-3-(3-methyl-5-isoxazolyl)methylene-1-azabicyclo[2.2.2]-octane oxalate in 28% yield. M.p. 134°–137° C. (Compound 1).

The next fractions contained the E isomer which after crystallization with oxalic acid gave (E)-3-(3-methyl-5-isoxazolyl)methylene-1-azabicyclo[2.2.2-]octane oxalate in 32% yield. M.p. 135°–136° C. (Compound 2).

EXAMPLE 2

The following compounds were prepared in exactly the same manner as described in example 1.

(Z)-6-(3-methyl-5-isoxazolyl)methylene-1-azabicyclo[3.2.1]octane oxalate, starting from 1-azabicyclo[3.2.1]octan-6-one and 3,5-dimethylisoxazole. M.p. 207°–209° C. (Compound 3).

(E)-6-(3-methyl-5-isoxazolyl)methylene-1-azabicyclo[3.2.1]octane oxalate, starting from 1-azabicyclo[3.2.1]octan-6-one and 3,5-dimethylisoxazole. M.p. 156°–157° C. (Compound 4).

(Z)-3-(3-methyl-5-isoxazolyl)methylene-1-azabicyclo[2.2.1]heptane oxalate starting from 1-azabicyclo[2.2.1]heptan-3-one and 3,5-dimethylisoxazole. M.p. 145°–146° C. (Compound 5).

(E)-3-(3-methyl-5-isoxazolyl)methylene-1-azabicyclo[2.2.1]heptane oxalate starting from 1-azabicyclo[2.2.1]heptan-3-one and 3,5-dimethylisoxazole. M.p. 161°–162° C. (Compound 6).

EXAMPLE 3

(Z) 3-(3-ethyl-1,2,4-oxadiazol-5-yl)methylene-1-azabicyclo[2.2.2]octane oxalate To a solution of sodium (50 mg, 1.7 mmol) in ethanol (5 ml) was added propionamid oxime (200 mg, 2 mmol) and (Z) 3-(ethoxycarbonylmethylene)-1-azabicyclo[2.2.2] octane (EP 0363085). The reaction mixture was heated at reflux for 6 h. Water (50 ml) was added and the water phase extracted with ether (3×50 ml). The combined organic extracts were dried over magnesium-sulphate and evaporated in vacuo. The residue was purified by column chromatography (eluent methylenechloride/methanol/ammoniumhydroxide: 80/20/0.5%) giving the free base in 170 mg yield. The free base was crystallized with oxalic acid from 2-propanol giving the title compound in 230 mg yield. M.p. 126°–127° C. (Compound 7).

In exactly the same manner the following compound was prepared:

(Z) 3-(3-methyl-1,2,4-oxadiazol-5-yl)methylene-1-azabicyclo[2.2.2]octane oxalate starting from acetamide oxime and (Z) 3-(ethoxycarbonylmethylene)-1-azabicyclo[2.2.2]octane. M.p. 146°–147° C. (Compound 8).

I claim:

1. A method of treating a disease caused by malfunctioning of the nicotinic cholinergic system other than Alzheimer's disease, Tourrette's syndrome, and severe pain in a subject in need thereof comprising administering to said subject an effective amount of a compound of formula I

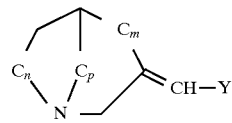

(I)

wherein p is 1 and either m is 0 and n is 1 or 2 or m is 1 and n is 1, or p is 2, m is 0 and n is 1; and wherein Y is

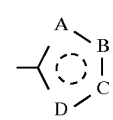

wherein

-A-B-C-D- is selected from
=C($R^1$)—O—N=C($R^2$)—, =C($R^1$)—S—N=C ($R^2$)—, =C($R^1$)—N=C($R^2$)—O—, =C($R^1$)—C($R^2$)=C($R^3$)—O—, =C($R^1$)—C($R^2$)=N—O—, =C($R^1$)—N=C($R^2$)—S—, =C($R^1$)—C($R^2$)=C($R^3$)—S—, =C($R^1$)—C($R^2$)=N—S—, —C($R^1$)=C($R^2$)—O—C($R^3$)=, —C($R^1$)=C($R^2$)—S—C($R^3$)=, —N($R^4$)—N=C($R^1$)—C($R^2$)=, =N—N($R^4$)—C($R^1$)=C($R^2$)—, =N—O—C($R^1$)=C($R^2$)—, =N—S—C($R^1$)=C($R^2$)—, —N($R^4$)—C($R^1$)=N—C($R^2$)=, —N=C($R^1$)—N($R^4$)—C($R^2$)=, =C($R^1$)—N($R^4$)—N=C($R^2$)—, —N=C($R^1$)—O—C($R^2$)=, —N=C($R^1$)—S—C($R^2$)=, =N—C($R^1$)=C($R^2$)—N($R^4$)—, =N—C($R^1$)=C($R^2$)—O—, =N—C($R^1$)=C($R^2$)—S—, —N($R^4$)—N=N—C($R^1$)=, =N—N($R^4$)—N=C($R^1$)—, —N=N—N($R^4$)—C($R^1$)=, —N($R^4$)—N=C($R^1$)—N=, =N—N($R^4$)—C($R^1$)=N—, =N—N=C($R^1$)—N($R^4$)—, =N—O—N=C($R^1$)—, =N—N=C($R^1$)—O—, =N—C($R^1$)—O—N=, =N—C($R^1$)=N—O—, =N—N=C($R^1$)—S—, =N—S—N=C($R^1$)—, =N—C($R^1$)=N—S—, —N=C($R^1$)—S—N=, —N($R^4$)—N=N—N= and =N—N($R^4$)—N=N—; and R$^1$, R$^2$ and R$^3$ independently are hydrogen, halogen, NR$^5$R$^6$, C$_{2-3}$-alkenyl, C$_{2-3}$-alkynyl or C$_{1-2}$-alkyl optionally substituted with one, two or three fluorine atoms; and R$^4$ is C$_{1-2}$-alkyl, cyclopropyl or propargyl; and R$^5$ and R$^6$ independently are hydrogen or methyl, or a pharmaceutically acceptable salt thereof.

2. The method according to claim 1 wherein -A-B-C-D- is selected from

=C(R1)—C(R2)=N—O—,
=C(R1)—C(R2)=N—S—,
=N—O—C(R1)=C(R2)—, and
=N—S—C(R1)=C(R2)—.

3. The method according to claim 1, wherein the compound is selected from the following:

(Z)-3-(3-methyl-5-isoxazolyl)methylene-1-azabicyclo[2.2.2]octane, (E)-3-(3-methyl-5-isoxazolyl)methylene-1-azabicyclo[2.2.2]octane, (Z)-6-(3-methyl-5-isoxazolyl)methylene-1-azabicyclo[3.2.1]octane, (E)-6-(3-methyl-5-isoxazolyl)methylene-1-azabicyclo[3.2.1]octane, (Z)-3-(3-methyl-5-isoxazolyl)methylene-1-azabicyclo[2.2.1]heptane, and (E)-3-(3-methyl-5-isoxazolyl)methylene-1-azabicyclo[2.2.1]heptane, or a pharmaceutically acceptable salt thereof.

4. The method of claim 1, wherein said disease is obesity.

5. The method of claim 1, wherein said disease is Parkinson's disease.

6. The method of claim 1, wherein said disease is anxiety.

7. The method of claim 1, wherein said disease is ulcerative colitis.

8. The method of claim 1, wherein the compound is administered as a pharmaceutical composition containing a pharmaceutically acceptable carrier or diluent.

9. The method of claim 8, wherein the pharmaceutical composition is an oral or parenteral dosage unit.

10. The method of claim 9, wherein said dosage unit comprises from about 1 to about 100 mg of a compound of claim 1.

* * * * *